(12) United States Patent
Sekino et al.

(10) Patent No.: US 9,067,798 B2
(45) Date of Patent: Jun. 30, 2015

(54) METHOD FOR PRODUCING SILICA-ZIRCONIA COMPOSITE PARTICLES EACH COATED WITH SILICA LAYER

(75) Inventors: Masato Sekino, Tokyo (JP); Masatsugu Kusano, Tokyo (JP)

(73) Assignee: Tokuyama Dental Corporation, Tokyo (JP)

( * ) Notice: Subject to any disclaimer, the term of this patent is extended or adjusted under 35 U.S.C. 154(b) by 115 days.

(21) Appl. No.: 13/387,163

(22) PCT Filed: Aug. 2, 2010

(86) PCT No.: PCT/JP2010/063025
§ 371 (c)(1),
(2), (4) Date: Jan. 26, 2012

(87) PCT Pub. No.: WO2011/016418
PCT Pub. Date: Feb. 10, 2011

(65) Prior Publication Data
US 2012/0121804 A1 May 17, 2012

(30) Foreign Application Priority Data
Aug. 7, 2009 (JP) .................................. 2009-184803

(51) Int. Cl.
| *C01B 33/12* | (2006.01) |
| *A61K 6/00* | (2006.01) |
| *A61K 6/02* | (2006.01) |
| *A61K 6/06* | (2006.01) |
| *C01G 25/00* | (2006.01) |
| *C01G 25/02* | (2006.01) |

(52) U.S. Cl.
CPC ............... *C01B 33/12* (2013.01); *A61K 6/0005* (2013.01); *A61K 6/0073* (2013.01); *A61K 6/024* (2013.01); *A61K 6/0612* (2013.01); *A61K 6/0681* (2013.01); *C01G 25/00* (2013.01); *C01G 25/02* (2013.01); *C01P 2002/50* (2013.01); *C01P 2004/62* (2013.01); *A61K 6/0052* (2013.01)

(58) Field of Classification Search
USPC ........................................... 427/215, 212, 213
See application file for complete search history.

(56) References Cited

FOREIGN PATENT DOCUMENTS

| JP | 2004-203683 A | 7/2004 |
| JP | 2007-269594 A | 10/2007 |
| JP | 269594 * | 10/2007 |
| JP | 2008-007381 A | 1/2008 |
| JP | 007381 * | 1/2008 |
| JP | 2008-37700 A | 2/2008 |

OTHER PUBLICATIONS

International Search Report dated Oct. 19, 2010, mailed Nov. 2, 2010.

* cited by examiner

*Primary Examiner* — Erma Cameron
(74) *Attorney, Agent, or Firm* — Norris McLaughlin & Marcus, P.A.

(57) ABSTRACT

Disclosed is a method for producing silica-zirconia composite oxide particles each coated with a silica layer, which is characterized in that a liquid dispersion of silica-zirconia composite oxide particles is obtained by reacting an alkoxide of silicon and/or a condensable compound derived from the alkoxide with an alkoxide of zirconium and/or a condensable compound derived from the alkoxide in a water-containing solvent that contains acetonitrile so that the reaction liquid is to contain not less than 10% by mass of acetonitrile, and then the surface of each silica-zirconia composite oxide particle is coated with a silica layer by reacting the silica-zirconia composite oxide particles dispersed in the liquid dispersion with an alkoxide of silicon and/or a condensable compound derived from the alkoxide in the liquid dispersion of silica-zirconia composite oxide particles.

4 Claims, No Drawings form a silica layer on each particle surface. Thereby, the present inventors tried to form silica layers on the surfaces of the silica-based composite oxide particles.

METHOD FOR PRODUCING SILICA-ZIRCONIA COMPOSITE PARTICLES EACH COATED WITH SILICA LAYER

TECHNICAL FIELD

The present invention relates to a method for producing silica-zirconia composite particles whose surfaces have been coated with a silica layer (the particles are hereinafter referred to as double-layered particles in some cases). With the present method, double-layered particles of high mono-dispersion can be produced under stable conditions.

BACKGROUND ART

There is known a method of producing spherical silica particles of high mono-dispersion by subjecting, for example, an alkoxide of silicon or the like, to hydrolysis and polycondensation. A method of producing metal oxide particles by subjecting an organic metal compound (e.g. metal alkoxide) as a raw material to polycondensation in a water-containing solvent, is generally called sol-gel processing. By using, as raw materials, an alkoxide of silicon and an alkoxide of a metal other than silica, silica-based composite oxide particles can be produced by the sol-gel processing. As the silica-based composite oxide particles, there are mentioned, for example, particles of silica-titania, silica-alumina, silica-zirconia, etc.

The silica-based composite oxide particles produced by the sol-gel processing are given characteristic properties depending upon the kind of the metal oxide contained in the particles together with silica. These characteristics are unobtainable with particles produced with silica alone.

The particles having such characteristics are in use in various applications. For example, by changing the mixing ratio of silica and a metal oxide other than silica, there can be obtained particles of desired refractive index while the optical transparency of the particles is maintained. By applying this technique, a transparent composite resin or a dental composite resin are obtained.

These composite resins, when using particles having a refractive index identical with those of the resins as filler, can show improved properties in mechanical strength, low thermal expansion, etc. while maintaining the visual transparency.

It is advantageous that the filler compounded in dental composite resin has radiopacity in addition to the above-mentioned transparency, from the standpoint of easy diagnosis of prognosis. Hence, as the filler compounded in dental composite resin, there are ordinarily used silica-based composite oxide particles which are a composite of silica and other metal oxide. As the other metal oxide in the silica-based composite oxide particles, there are preferred titania, zirconia, barium oxide, etc. all having Radiopacity. By controlling the compounding ratio of such a metal oxide to make the refractive index of filler identical with that of resin, there can be obtained a dental filler having both transparency and Radiopacity.

Meanwhile, in producing silica-based composite oxide particles by the above-mentioned sol-gel processing, there has ordinarily been a problem that silica-based composite oxide particles formed tend to coagulate. Further, fresh silica-based composite oxide particles are incessantly formed with the passage of time and this causes a problem that the diameters of the particles formed become non-uniform. These phenomena are striking as the content of the metal oxide other than silica in composite oxide particles is higher. This makes it difficult to obtain silica-based composite oxide particles of high mono-dispersion and uniform particle diameter.

For producing silica-based composite oxide particles of high mono-dispersion, there was proposed a method of using water-containing acetonitrile in the reaction mixture of sol-gel processing (reference is made to Patent Literature 1). In the method, the concentration of acetonitrile in the reaction mixture is at least 20% by mass. The method is very effective for solving the above problems and, in fact, can efficiently produce silica-based composite oxide particles of high mono-dispersion.

PRIOR ART LITERATURE

Patent Literature

Patent Literature 1: JP 2007-269594 A

DISCLOSURE OF THE INVENTION

Technical Problem

It is preferred that the silica-based composite oxide particles produced by the above method or the like are coated at each surface with a silica layer to take a form of double-layered particle. Such double-layered particles are particularly useful, for example, when used as a filler in dental composite resin. Generally, the above-mentioned silica-based composite oxide particles, unlike particles constituted by silica alone, have, at the surfaces, strongly acidic points owing to the metal oxide forming the composite oxide together with silica. When such particles each having this acidic point are compounded in a dental composite resin, the acid point causes the denaturation of the resin matrix moiety constituting the composite resin and the coagulation of filler. Further, the acid point promotes the adsorption of the minor amount components (e.g. pigment, polymerization initiator and polymerization inhibitor) contained in the composite resin; as a result, the functions of these components are not exhibited sufficiently. Accordingly, coating of the surface of each silica-based composite oxide particle with an inactive silica layer is extremely effective for reducing the activity of acidic point.

Meanwhile, the present inventors found that the coating of the surface of each silica-based composite oxide particle with a silica layer was difficult even in the case of the silica-based composite oxide particle obtained by the sol-gel processing using a reaction mixture containing acetonitrile.

In order to coat the surface of silica-based composite oxide particle with a silica layer, the present inventors reacted an alkoxide of silicon successively in the same reaction mixture. In this case, the mono-dispersion of the particles in the reaction mixture deteriorated rapidly and the coagulation of particles was striking. The coagulation was particularly striking when the content of metal oxide other than silica in the silica-based composite oxide particles each coated with a silica layer was 10 mol % or higher.

Such situation that stable production of double-layered particles with high mono-dispersion is impossible, is a big problem industrially.

Hence, the task of the present invention is to develop a method for stably producing, without causing coagulation of formed particles in the reaction mixture, silica-based composite oxide particles coated, at the surfaces, with a silica layer (therefore, the particles are double-layered particles), which have both transparency and Radiopacity and are useful as a filler compounded in dental composite resin.

Technical Solution

The present inventors made a study in order to achieve the above task. That is, the present inventors made a study on production of silica-based composite oxide particles using an alkoxide of silicon and an alkoxide of a metal other than silicon and subsequent coating of the surface of each silica-based composite oxide particle produced, with a silica layer. As result, it was confirmed that, when silica-based composite oxide particles were produced in an aqueous solvent containing acetonitrile and then a silica layer was coated on the surface of each particle, the double-layered particles obtained tended to cause coagulation very easily during the reaction and after the reaction.

The present inventors made a further study on the coating of silica layer on particle surface. As a result, it was found that a silica layer could be coated on the surface of each oxide particle in a state that the dispersibility of double-layered particles obtained was kept at a very high level, only in the case of silica-based composite oxide particles in which the metal other than silicon was zirconium.

That is, the present inventors found that, when there was used a liquid dispersion of silica-based composite oxide particles produced in an aqueous solvent containing acetonitrile and a silica layer was coated on the surface of each composite oxide particle in the liquid dispersion, the coagulation of the composite oxide particles was prevented strikingly only when the composite oxide particles were silica-zirconia composite oxide particles. As a result, it was confirmed that, in coating silica-zirconia composite oxide particles, silica-zirconia composite oxide particles each coated with a silica layer could be produced very efficiently. The above studies have led to the completion of the present invention.

The present invention lies in a method for producing silica-zirconia composite oxide particles each coated with a silica layer, which method is characterized by reacting an alkoxide of silicon and/or a condensable compound derived from the alkoxide with an alkoxide of zirconium and/or a condensable compound derived from the alkoxide in a water-containing solvent that contains acetonitrile so that the reaction mixture contains at least 10% by mass of acetonitrile, to produce a liquid dispersion of silica-zirconia composite oxide particles, and then reacting the silica-zirconia composite oxide particles dispersed in the liquid dispersion with an alkoxide of silicon and/or a condensable compound derived from the alkoxide in the liquid dispersion of silica-zirconia composite oxide particles, to coat the surface of each silica-zirconia composite oxide particle with a silica layer.

Advantageous Effects

The present invention is a method for producing silica-zirconia composite oxide particles each coated with a silica layer. With the present method, it is impossible to produce composite oxide particles containing a metal oxide other than zirconia, each coated with a silica layer.

The silica-zirconia composite oxide particles each coated with a silica layer, produced by the present method have excellent Radiopacity. Further, the silica-zirconia composite oxide particles each coated with a silica layer can have a refractive index identical with that of resin by controlling the compounding ratio of silica and zirconia. Accordingly, the silica-zirconia composite oxide particles each coated with a silica layer, produced by the present method can be utilized as a filler having both human visual transparency and Radiopacity. This filler is useful as, for example, a filler compounded in dental composite resin.

Silica-zirconia composite oxide particles each have an acidic point on the surface. Therefore, the silica-zirconia composite oxide particles are highly active at the surfaces. In contrast, the silica-zirconia composite oxide particles each coated with a silica layer, produced by the present method are each coated with a silica layer over the acidic surface and accordingly are inactive. According to the present method, silica-zirconia composite oxide particles each coated with a silica layer and having an inactive surface can be produced stably without causing the coagulation of particles.

BEST MODE FOR CARRYING OUT THE INVENTION

The production method of the present invention comprises
a first reaction step of producing silica-zirconia composite oxide particles, and
a second reaction step of coating the surface of each silica-zirconia composite oxide particle obtained in the first reaction step, with a silica layer.
(First Reaction Step)

The first reaction step is basically the same as the conventional method of producing silica-zirconia composite oxide particles by the sol-gel processing. That is, a raw material for silica and a raw material for zirconia are added into a water-containing solvent and they are reacted.

The present invention is characterized in that the first reaction step of producing silica-zirconia composite oxide particles is conducted in a state that acetonitrile is present at a predetermined concentration during the reaction.

In the present production method, the first reaction step is conducted in a water-containing solvent which contains acetonitrile so that the reaction mixture contains at least 10% by mass of acetonitrile. Incidentally, the reaction mixture refers to a mixture containing all components of reaction solvent at the start of reaction (this is a water-containing organic solvent and, when composite oxide particles have been formed, functions also as a dispersing agent), catalyst, solid component formed by reaction (silica-based composite oxide particles), by-products (e.g. alcohol) formed by reaction, unreacted reaction raw materials remaining in reaction system, water and organic solvent as necessary added during the reaction, etc. The above-mentioned concentration of acetonitrile is based on the total mass of the above-mentioned reaction mixture.

When the first reaction step of producing silica-zirconia composite oxide particles is conducted in a state that acetonitrile is contained in the reaction mixture at the above-mentioned concentration, the silica-zirconia composite oxide particles formed is strikingly prevented from coagulating. As a result, there can be obtained a liquid dispersion of silica-zirconia composite oxide particles of excellent mono-dispersion.

As mentioned above, the coagulation of particles is prevented strikingly in the second reaction step only when zirconium is selected as other metal used together with silica for production of composite oxide particles. The reason therefor is not clarified yet. The present inventors consider as follows. In general, a polycondensation reaction in which zirconium takes part, proceeds mildly, as compared with a reaction in which other metal oxide takes part; this mild reaction and the prevention of coagulation due to the use of acetonitrile act synergistically on each other; as a result, the second-stage reaction proceeds mildly, contributing to the prevention of coagulation.

When silica-based composite oxide particles are produced by the sol-gel processing as mentioned above, the surface potential of the particles drops as the content of metal oxide other than silica is higher. As a result, the repulsion between particles becomes insufficient and the particles coagulate with each other easily. For the above reason, the higher content of metal oxide other than silica in silica-based composite oxide particles makes it impossible to obtain particles of high mono-dispersion.

Further, the coagulation phenomenon becomes more striking in proportion to the dispersion amount of silica-based composite oxide particles formed. It is because the repulsion energy between particles decreases and the surface potential of each particle decreases further.

Prevention of the decrease in surface potential of particle can be expected by conducting the reaction in a solvent (or dispersing medium) containing an aprotic polar solvent at a high concentration. An aprotic polar solvent does not function as an electrolyte. The aprotic polar solvent donates no proton to other substance; accordingly, it is expected that the aprotic solvent coordinates to particles, strengthening the electric repulsion between particles. However, no large coagulation prevention effect such as expected by the above reason is obtained when there is used an aprotic polar solvent other than acetonitrile, such as dimethyl sulfoxide, dimethylformamide or the like. The excellent effect of coagulation prevention is uniquely possessed by acetonitrile.

The effect of coagulation prevention possessed by acetonitrile is exhibited by maintaining the concentration of acetonitrile in reaction mixture at least 10% by mass. The effect of coagulation prevention to particles, caused by the acetonitrile added into the reaction mixture of first reaction step is particularly high when the other metal oxide used together with silica in composite oxide particles is zirconium. Accordingly, the effect of coagulation prevention to particles is good even when the content of acetonitrile is relatively small, for example, slightly above 10% by mass.

However, the dispersibility of particles is strikingly inferior when there are produced silica-zirconia composite oxide particles containing zirconia of 10 mol % or more. When there are produced particles which coagulate easily as mentioned above, or particles of high mono-dispersion and very good roundness, the concentration of acetonitrile is preferably 15 to 85% by mass, more preferably 15 to 60% by mass.

In the present production method, when particles of zirconia content of 10 mol % or more are produced in a state that the concentration of acetonitrile in the reaction mixture of first reaction step is kept at 10% by mass or higher, the obtained silica-zirconia composite particles each coated with a silica layer (i.e. double-layered particles) have a fluctuation coefficient of particle diameters, of ordinarily 8% or less. The double-layered particles have a roundness of ordinarily 0.7 or more. Further, when the concentration of acetonitrile is kept at 15 to 90% by mass, the obtained double-layered particles have a fluctuation coefficient of particle diameters, of ordinarily 7% or less and a roundness of ordinarily 0.8 or more.

Incidentally, the shape of silica-based composite oxide particles or silica-zirconia composite oxide particles each coated with a silica layer can be observed using, for example, a scanning or transmission electron microscope. The average particle diameter of these particles can be determined by analyzing the photographed image of scanning electron microscope using an image analyzer, measuring the particle diameter of each of at least 200 particles in the image, and calculating the average of the measured particle diameters.

The mono-dispersion of particles (the fluctuation coefficient of particle diameters) is indicated by the ratio of the above-obtained average particle diameter of 200 particles and the standard deviation thereof.

The roundness of particle is a parameter indicating the closeness of particle to sphere. The roundness is indicated by $(4\pi \times S)/L^2$ wherein S is the projected area of particle observed by scanning or transmission electron microscope and L is the circumferential length of particle.

In the first reaction step, the concentration of acetonitrile in reaction mixture is preferably high at the beginning of reaction. The concentration of acetonitrile at the start of reaction is preferably at least 20% by mass, more preferably at least 30% by mass, particularly preferably 40 to 80% by mass.

During the reaction, raw materials (raw material for silica and raw material for zirconia) and, as necessary, ammonia water, etc. are fed. As a result, the concentration of acetonitrile in reaction mixture reduces gradually from the concentration at the start of reaction. In order to keep the acetonitrile concentration at least 10% by mass, there is used, for example, a reaction mixture containing a sufficient amount of acetonitrile at the start of reaction, in view of the fed amounts of raw materials, etc., or, acetonitrile is fed intermittently or continuously during the reaction so that the acetonitrile concentration can be kept in a predetermined range during the reaction.

The reaction of raw material for silica and raw material for zirconia is the same as when silica-based composite oxide particles are produced by the conventional sol-gel processing, except that the acetonitrile concentration is kept, during the reaction, at least at 10% by mass in the reaction solvent containing acetonitrile. As the reaction agent, a reagent conventionally used can be used with no particular restriction.

As to the average particle diameter of the silica-zirconia composite oxide particles formed, at the end of the first reaction step, there is no particular restriction. However, the average particle diameter is ordinarily 0.05 to 1.0 µm, preferably 0.08 to 0.5 µm. When particles having an average particle diameter exceeding 1.0 µm are produced, much time is taken in order to grow particles and new nuclei of particles are generated easily in the course of production. As a result, production of composite oxide particles of high mono-dispersion tends to be difficult. When particles having an average particle diameter smaller than 0.05 µm are produced, the particles have high mono-dispersion. However, the silica-zirconia composite oxide particles each coated with a silica layer, produced with such particles are inferior in handleability and tend to cause coagulation in the drying or firing step conducted later as necessary.

The raw material for silica, used in the first reaction step is
(1) an alkoxide of silicon, represented by the general formula $Si(OR)_4$ or $SiR'_n(OR)_{4-n}$ wherein R and R' are each an organic group which may contain an ether bond or an ester bond, and n is an integer of 1 to 3),
(2) a low-condensation product obtained by partial hydrolysis of the above-mentioned alkoxide of silicon (the low-condensation product is a condensable compound having an alkoxy group or a hydroxyl group in the molecule), or
(3) a mixture of (1) and (2).

In the alkoxide of silicon, represented by the above general formula, the plurality of R's contained in the molecule may be the same or different from each other. For high availability, there is ordinarily preferred a compound in which the plurality of R's in the molecule are the same organic group. As the organic groups of R and R', an alkyl group is preferred for easy availability of the raw material having such an organic group. R and R' are preferred to be a lower alkyl group such as methyl group, ethyl group, isopropyl group, butyl group or the like, because the raw material having such a group has good compatibility with an organic solvent and, moreover, the alcohol formed by hydrolysis has a low boiling point and is easily removed from the particles formed.

An alkoxide of zirconia is used as the raw material for zirconia, with no particular restriction.

Specifically, there can be preferably used an alkoxide obtained by replacing the Si in the above-mentioned general formula of the alkoxide of silicon, with Zr; a low-condensation product obtained by partial hydrolysis of the alkoxide of zirconia (this low-condensation product is also a condensable compound); or a mixture thereof.

The zirconia content in the silica-zirconia composite oxide particles formed in the first reaction step is determined appropriately depending upon the application purpose of the particles. When the particles are used as a filler compounded in a dental composite resin, the content of zirconia is determined in view of the transparency and Radiopacity. The content of zirconia is generally preferably 5 to 30 mol %. In order to obtain the effect of the present invention, i.e. the prevention of particle coagulation to be exhibited more strikingly, the zirconia content is preferably 10 mol % or higher, more preferably 11 to 20 mol %.

Incidentally, the silica-zirconia composite oxide particles produced in the first reaction step of the present invention may not necessarily be constituted by silica and zirconia only. The particles may contain a small amount of other metal oxide as long as the excellent properties of silica-zirconia composite oxide particles are maintained.

As the metal oxide other than silica and zirconia, there can be mentioned oxides of metals of group 1, group 2, group 3, group 4 (excluding zirconia), and group 13 of periodic table. Specifically, there can be mentioned lithium, sodium, magnesium, calcium, strontium, barium, scandium, yttrium, titanium, hafnium, aluminum, lanthanoid, actinoid, etc. Of these metal oxides other than silica and zirconia, oxides of alkali metals are preferred because the addition of small amount can easily neutralize the acidic point of surface; and sodium oxide is preferred particularly.

A method for allowing such an other metal oxide to be contained in silica-zirconia composite oxide particles, there is used, in the first reaction step, an alkoxide of a metal other than silica and zirconia, a low-condensation product obtained by partial hydrolysis of the alkoxide (the low-condensation product is also a condensable compound), or a mixture thereof, as a raw material for composite oxide particles, other than the raw material for silica and the raw material for zirconia. Generally, the content of the metal oxide other than silica and zirconia is preferably 5 mol % or less, more preferably 3 mol % or less relative to the total metal oxides constituting the composite oxides particles.

In the first reaction step of the present invention, a reaction is conducted by adding the raw material for silica, the raw material for zirconia, etc. into a reaction solvent containing water, acetonitrile, an organic solvent, etc. Preferably, a catalyst is added into the reaction mixture in order to promote a hydrolysis reaction and a polycondensation reaction.

As to the catalyst, there is no particular restriction as long as the catalyst has a function for promoting the hydrolysis and polycondensation of metal alkoxide. Ordinarily, an acid or a base is usable. Use of a base catalyst is preferred because it enables production of spherical particles of high mono-dispersion.

As examples of the base catalyst preferably used in the present invention, there can be mentioned inorganic bases such as ammonia, lithium hydroxide, sodium hydroxide, potassium hydroxide and the like; and organic bases such as methylamine, dimethylamine, trimethylamine, ethylamine, diethylamine, triethylamine, propylamine, dipropylamine, tripropylamine, pyridine, imidazole, piperidine, quinoline, pyrrole, 1,4-diazabicyclo[2.2.2]octane, 1,8-diazabicyclo[5.4.0]unde-7-cene, tetramethylammonium hydroxide and the like. Of these, a metal-free base such as ammonia, amine or the like is used preferably. The silica-based oxide particles produced are dried or fired in the post-treatment, in some cases. The above catalyst is preferred particularly because, with such a catalyst, no base component or no metal component remains in the particles after the post-treatment.

The addition amount of the catalyst differs depending upon the kind of the catalyst used and the kinds and proportions of water, organic solvent, etc. in reaction mixture. It is preferred generally that the catalyst is added so that the pH of reaction mixture becomes 10 or more, preferably 11 or more. Incidentally, gradual addition of raw materials into reaction mixture invites an increase in the amount of reaction mixture and a resultant change in the concentration of catalyst. In such a case, it is preferred that the catalyst is supplemented continuously or intermittently so that the pH of the reaction mixture is kept in the above range during the reaction.

When ammonia is used as the most preferable catalyst, it is preferred that ammonia is allowed to be present at a concentration of 2 to 20% by mass, preferably 3 to 15% by mass relative to the mass of the reaction mixture, from the start of first step reaction to the end of second step reaction. Here, the mass of the reaction mixture is specifically the mass of the total reaction mixture containing an organic solvent (containing initially fed water), fed raw materials, fed catalyst, etc.

In the first reaction step, there is no particular restriction as to the reaction solvent as long as it is a solvent containing water and acetonitrile of above-mentioned concentration. There is no particular restriction as to the concentration of water, but the all components excluding acetonitrile and catalyst may be water. In order for the hydrolysis and polycondensation to be carried out successfully, the content of water in reaction mixture is at least the theoretical amount necessary for the hydrolysis and polycondensation of the fed total amounts of the raw material for silica and the raw material for zirconium. That is, water is added in the reaction solvent at an amount of at least ½ mol of the total alkoxide groups possessed by the raw materials.

A water-soluble organic solvent may be added into the reaction solvent. As the water-soluble organic solvent, there can be mentioned alcohols such as methanol, ethanol, propanol, isopropanol, butanol, isobutyl alcohol, ethylene glycol, propylene glycol and the like; ketones such as acetone, methyl ethyl ketone and the like; ethers such as dioxane, tetrahydrofuran and the like; esters such as ethyl acetate and the like; and so forth. As the reaction solvent, there are preferred lower alcohols of 1 to 4 carbon atoms, such as methanol, ethanol, isopropanol and the like. These water-soluble organic solvents are preferred because they have good compatibility with metal alkoxides and water and have a low viscosity and because they have a function to keep a small average particle diameter of the composite oxide particles obtained easily.

During the reaction, the acetonitrile in the reaction solvent is diluted by the raw materials fed (raw material for silica, raw material for zirconia, and the ammonia water fed as necessary, etc.). Accordingly, it occurs that the acetonitrile concentration decreases from the concentration at the start of reaction to a lower concentration. In order to keep the acetonitrile concentration in the reaction mixture at least 10% by mass, it is preferred that the addition amount of acetonitrile is controlled beforehand in view of the increase in mass, of raw materials, etc. As a specific measure, it is considered to use, as the reaction solvent used at the start of reaction, a reaction solvent containing a sufficient amount of acetonitrile. Or, in order to keep the acetonitrile concentration in reaction mixture at least at 10% by mass, acetonitrile is fed into the reaction mixture intermittently or continuously during the reaction.

In the first reaction step, the raw materials are added into an organic solvent to give rise to a reaction. This reaction is the same as in the conventional sol-gel processing. In order to produce silica-zirconia composite oxide particles of good properties, it is preferred method that a raw material for silica and a raw material for zirconia are mixed beforehand and the mixture is added into a reaction solvent.

When an alkoxide of silicon is used as the raw material for silica, it is preferred that, prior to the above mixing, part or all of the alkoxide of silicon is subjected to hydrolysis (hereinafter, this hydrolysis is referred to also as partial hydrolysis). With this approach, more homogeneous composite oxide particles are obtained. In the partial hydrolysis, it is preferred to use, together with water, an organic solvent (e.g. alcohol) having compatibility with both the alkoxide and water. Addition of a catalyst in the partial hydrolysis enables rapid progress of the partial hydrolysis. The catalyst is preferably an acid. Specifically, there can be mentioned hydrochloric acid, sulfuric acid, nitric acid, succinic acid, etc., but there is no particular restriction. With respect to the concentration of the acid, use of an acid of pH 1 to 4 is preferred.

In mixing method of the raw material for silica and the raw material for zirconia, it is preferred that each raw material is weighed in accordance with the composition of the silica-based composite oxide particles produced and the two materials are mixed. By employing this mixing method, composite alkoxides of the two raw materials are formed. As a result, silica-zirconia composite oxide particles having a small fluctuation coefficient of particle diameters can be produced efficiently. Incidentally, when the alkoxide of silicon is subjected to partial hydrolysis beforehand, the partial hydrolysis product obtained is mixed with the raw material for zirconia.

The first reaction step may be conducted other than the procedure mentioned above, unless the gist of the present invention is changed. For example, raw materials may be added separately into a reaction solvent to give rise to a reaction.

In the first reaction step, it is preferred that the raw materials are fed so that the concentration of silica-zirconia composite oxide particles in reaction mixture at the completion of the reaction for formation of the particles becomes as high as 5 to 30% by mass, preferably 7 to 20% by mass, more preferably 7 to 15% by mass, particularly preferably 10 to 15% by mass.

The raw materials are a raw material for silica and a raw material for zirconia, as mentioned previously. Together with these raw materials, there is used, as necessary, a raw material for other metal oxide, other than the raw material for silica and the raw material for zirconia, as long as the use does not impair the effect of the present invention.

As mentioned previously, the coagulation of silica-zirconia composite oxide particles becomes more striking as the concentration of the particles becomes higher. Owing to this easy coagulation of particles, the coagulation of particles becomes more striking also when the particles are coated with a silica layer in the second reaction step. Therefore, the effect (i.e. prevention of coagulation) of the present invention is exhibited particularly remarkably when the particles concentration in the liquid dispersion is high.

When, in the first reaction step, the concentration of silica-based composite oxide particles in reaction mixture is lower than 5% by mass at the completion of reaction of particles formation, the extent of the coagulation of the particles is considerably low up to the completion of the second reaction step. Incidentally, there is no noticeable deterioration in mono-dispersion of particles even when the other metal oxide used in composite metal particles together with silica is other than zirconia.

When the concentration of silica-based composite oxide particles in reaction mixture is higher than 30% by mass at the completion of reaction of particles formation, the coagulation of particles becomes striking even when the other metal oxide is zirconia. As a result, it is difficult to prevent coagulation even by controlling the concentration of acetonitrile in the previously-mentioned range.

In order to form silica-zirconia composite oxide particles at a high concentration in the reaction mixture, it is appropriately conducted, for example, to feed large amounts of raw materials into the reaction mixture or to take a long reaction time. Particularly preferably, the concentrations of raw materials are made high in the reaction mixture and the amount of the reaction mixture is made small.

By conducting a reaction under such conditions, silica-zirconia composite oxide particles, having an average particle diameter of 0.1 to 1.0 μm are formed in the reaction mixture in the above-mentioned concentration range.

In adding raw materials into a reaction solvent, the raw materials may be diluted with an organic solvent such as alcohol, acetonitrile or the like and then be added into the reaction solvent. However, in order to increase the concentration of composite oxide particles formed, in the reaction mixture, it is desired to add the raw materials with no dilution, or, when dilution is made, to use a dilution ratio of 30% by mass or lower, particularly preferably 10% by mass or lower.

In adding the raw materials into a reaction solvent, it is preferred that the raw materials are dropped into the reaction solvent (in-liquid dropping) because the in-liquid dropping makes less likely to cause the coagulation of particles. The in-liquid dropping refers to the feeding of raw materials into a reaction solvent in a state that the front end of raw material-feeding pipe (the discharge hole of raw material) is immersed in the reaction solvent. The position of the discharge hole is not particularly restricted as long as it is in the reaction solvent. The position of the discharge hole is desirably a position at which stirring is made sufficiently, for example, the vicinity of agitating blade.

Preferred as the catalyst is a basic catalyst such as ammonia or the like. As the aqueous alkaline solution containing the basic catalyst, there is preferred ammonia water of 10 to 30% by mass.

The addition of the catalyst is conducted preferably by dropping an aqueous alkaline solution prepared separately, into the reaction mixture simultaneously with the dropping of raw materials. The dropping of the aqueous alkaline solution need not necessarily be this in-liquid dropping. However, the in-liquid dropping of the aqueous alkaline solution at the vicinity of agitating blade is preferred because stirring in the reaction mixture can be made sufficiently. Thus, by dropping the aqueous alkaline solution simultaneously with the raw materials, the amount of alkali in reaction vessel can be kept constant throughout the reaction period. As a result, the reaction rate is kept high throughout the reaction period. That is, the concentration of the reaction substrate generated by alkali is kept high. Consequently, particles can be synthesized at a high solid content, making possible the synthesis of high yield (high productivity).

Incidentally, in the simultaneous dropping of aqueous alkaline solution, it is preferred that the aqueous alkaline solution is dropped so that the mols of water in aqueous alkaline solution fed are 1 to 6 times, preferably 2 to 5 times the total mols of metals (silicon and zirconia) in the raw materials fed simultaneously.

The dropping rate of raw materials is preferably small in order to obtain composite oxide particles of high mono-dispersion. However, with too small a dropping rate, a long time is taken by the completion of the first reaction step. Accordingly, it is preferred that the dropping rate is small at the initial stage of the step and is high at the latter half of the step.

Preferably, the raw materials and the aqueous alkaline solution are dropped continuously from the start of the dropping to the completion of the dropping. Incidentally, "continuously" referred to herein means that there is no time interval of preferably 10 minutes or longer, more preferably 3 minutes or longer. The dropping rate need not necessarily be constant; however, when the dropping rate is varied, the variation is made continuously, desirably. When they are fed intermittently with time intervals being taken, the atmosphere in reaction mixture is disturbed by the rapid addition of water, which may cause the coagulation of particles, the generation of fresh particle nuclei, etc.

The reaction temperature is set appropriately depending upon the kinds of raw materials used. It is ordinarily 0 to 50° C. The reaction proceeds rapidly after the feeding of raw materials. Hydrolysis is followed by polycondensation (ordinarily, condensation by alcohol removal), whereby a Si—O—Si bond and a Si—O—Zr bond are formed and, resultantly, silica-zirconia composite oxide particles are formed.

In the first reaction step of forming silica-zirconia composite oxide particles, stirring is made for 0.5 to 2 hours after the addition of all raw materials into reaction mixture, and further for about 1 to 60 minutes as necessary, to complete the reaction. Then, the liquid dispersion of silica-zirconia composite oxide particles obtained is sent to the second reaction step described below.

(Second Reaction Step)

In the second reaction step, it is preferred that the liquid dispersion of composite oxide particles, obtained in the first reaction step is used per se and the surface of each composite oxide particle is coated with a silica layer in the reaction mixture.

Specifically explaining, an alkoxide of silicon and/or a condensable compound derived from the alkoxide is subjected to hydrolysis and polycondensation in the liquid dispersion of silica-zirconia composite oxide particles.

As mentioned previously, there is a case, in the first reaction step, that composite oxide particles of silica and a metal oxide other than zirconia are produced as silica-based composite oxide particles, by converting silica and a metal oxide (e.g. titanium, alumina or borane) other than zirconia into a composite oxide. In this case, a liquid dispersion of particles, of high mono-dispersion may be obtained by the effect of acetonitrile use. Even in this case, when a second reaction step is conducted using this liquid dispersion of particles, of high mono-dispersion, the particles obtained are ordinarily reduced strikingly in mono-dispersion when the particles are other than silica-zirconia composite oxide particles, and the coagulation of particles ordinarily takes place strikingly.

The mechanism of the coagulation of particles is not clarified yet, but the present inventors consider as follows.

At the end of the first reaction step, the feeding of raw materials is stopped to once complete the reaction. Then, the second reaction step is restarted. However, in the second reaction step, the reaction is started under conditions different from those in the previous step. In the second step, particles are considered to coagulate easily until the reaction mixture is stabilized. In this state, a small amount of particles gives rise to coagulation; these particles become nuclei; and coagulation proceeds during the whole period of second reaction step. Further, partial disintegration, etc. of the particles which have coagulated, takes place. Resultantly, the above-mentioned striking reduction in mono-dispersion takes place.

Meanwhile, the appearance of particle coagulation is prevented greatly in the second reaction step as well when, as in the present method, silica-zirconia composite oxide particles are produced as silica-base composite oxide particles.

The reason is not clear. However, the present inventors consider as follows.

The reaction of silica-zirconia system in the first reaction step is mild; therefore, the surfaces nature of the composite oxide particles obtained are less likely to cause particle coagulation as compared with composite oxide particles of silica and metal oxide other than zirconia.

As the start of the second reaction step, acetonitrile is contained in the liquid dispersion of silica-zirconia composite oxide particles in an amount of at least 10% by mass. Therefore, the second reaction step of coating by a silica layer is conducted continuously from the first reaction step, in the above liquid dispersion of silica-zirconia composite oxide particles. In this case, the coating reaction is complete in a short time as compared with the first reaction step. As a result, an intended coating reaction can be allowed to proceed in a state that the effect of good coagulation prevention by acetonitrile is kept satisfactorily.

For example, even when the second reaction step is conducted with no supplementation of acetonitrile and accordingly the acetonitrile concentration is slightly lower than 10% by mass (not lower than 7% by mass is preferred) in the course of the reaction, the coagulation of particles can be allowed to remain at an allowable low level. Of course, the mono-dispersion of particles obtained in the second reaction step is much higher when, in the second reaction step, acetonitrile is supplemented as necessary together with the feeding of raw material for silica and the acetonitrile concentration is kept within the above-mentioned specified range (at least 10% by mass, preferably 15 to 85% by mass).

As the raw material used for coating by silica layer, there can be used the raw material for silica used as a raw material for silica-zirconia composite oxide particles in the first reaction step. The catalyst used is also the same as used in the first reaction step. The second reaction step is carried out while appropriately supplementing the short amount of the catalyst in view of the catalyst amount remaining in the liquid dispersion of silica-zirconia composite oxide particles. The second reaction step is carried out while also supplementing the short amount of water as necessary.

Besides, the method of feeding raw materials and the reaction conditions (e.g. reaction temperature) are the same as descried in the first reaction step.

The thickness of the silica layer formed on the surface of each silica-zirconia composite oxide particle is preferably 5 to 30 nm, more preferably 5 to 25 nm, in view of the balance between the sufficient coating of acidic points and the radiopacity and transparency possessed by silica-zirconia composite oxide particles.

The coating of the surface of each silica-zirconia composite oxide particle with silica layer is conducted, for example, by reacting the silica-zirconia composite oxide particles in the reaction mixture and a raw material for silica (e.g. an alkoxide of silicon), directly, or after dilution in a solvent, or after partial hydrolysis. As the raw material for silica, preferred is, as in the first reaction step, a substance represented by the general formula $Si(OR)_4$ or $SiR'_n(OR)_{4-n}$.

The second reaction step is the same as the first reaction step. That is, all raw materials are fed into the liquid dispersion and then stirring is made for about 1 to 30 minutes as necessary, to complete the reaction. After the reaction, the silica-zirconia composite oxide particles each coated with a silica layer, i.e. the double-layered particles, are preferably isolated from the reaction mixture. The isolation operation is conducted by solid-liquid separation, using centrifugation, filtration, vacuum distillation, spray-drying, or the like. It is possible that the reaction solvent is replaced by an organic solvent such as water, alcohol or the like and the double-layered particles are stored in the form of a liquid dispersion thereof. There is no particular restriction as to the method for replacement of solvent. For example, it is possible that the double-layered particles are taken out in the form of a powder and a desired solvent is added to redisperse the double-layered particles in the solvent. Or, it is possible that the reaction mixture after the second reaction step is concentrated by ultrafiltration or the like, then a desired solvent is added, and this operation is repeated, whereby replacement of solvent is conducted.

The powder of double-layered particles, obtained by production of double-layered articles and subsequent separation from solvent may be further dried. The drying temperature is preferably 50 to 300° C. The drying time is several hours to several days. The dried powder may be fired at a higher temperature. The firing temperature is preferably 300 to 1,300° C. and the firing time is preferably 1 to 24 hours. The dried or fired double-layered particles can be disintegrated using a grinder such as ball mill, jet mill or the like. When the double-layered particles are dispersed in a resin or the like using a dispersing machine of high shear, dispersion in resin and disintegration of particles can be conducted simultaneously.

The fluctuation coefficient of particle diameters and the roundness of each particle, both possessed by the silica-zirconia composite oxide particles produced in the first reaction step, are ordinarily kept at preferred levels with the silica-zirconia composite oxide particles each coated with a silica layer, produced in the second reaction step.

The silica-zirconia composite oxide particles each coated with a silica layer, produced by the present invention are useful particularly as a filler in dental composite resin. The particles are also useful as an additive in anti-reflection layer, transparent resin of high refractive index, film, etc.

EXAMPLES

The present invention is specifically described below by way of Examples. However, the present invention is in no way restricted by these Examples.

Properties of double-layered, silica-based composite oxide particles were measured as follows.
(1) "Average Particle Diameter", "Fluctuation Coefficient of Particle Diameters" and "Roundness"

These properties were obtained by randomly selecting 200 particle images from the photographed image of scanning electron microscope and analyzing the images using an image analyzer. Here, "average particle diameter" refers to an average of the 200 particle diameters obtained by the image analysis, and "fluctuation coefficient of particle diameters" was calculated using the following formula.

Fluctuation coefficient(%)=(standard deviation of particle diameters/average particle diameter)×100

Roundness=$(4\pi \times S)/L^2$

Here, S is the projected area of particle and L is the projected circumferential length of particle.

"Roundness" is a parameter indicating the closeness of particle to sphere.
(2) Refractive Index The refractive index of particles was measured by in-liquid immersion method. That is, various solvents of different refractive indices (e.g. toluene, 1-bromonaphthalene, 1-chloronaphthalene, diiodomethane and sulfur-containing diiodomethane) were mixed appropriately to prepare mixed solvents of various refractive indices. Particles were dispersed in each of the mixed solvents each having a different refractive index, to prepare various liquid dispersions of particles. The liquid dispersions were measured for refractive index at 25° C. and the refractive index of the most transparent liquid dispersion was taken as the refractive index of the particles. The refractive index of each mixed solvent was measured at 25° C. using an Abbe refractometer.
(3) Crystal Form The crystal form of particles was identified using an X-ray diffractometer.
(4) Thickness of Coated Silica Layer The thickness of coated silica layer was obtained by observing particles using a transmission electron microscope, taking the photograph thereof, selecting 10 particle images randomly from the photograph, and analyzing the images.
(5) Concentration of Particles 10 g of a liquid dispersion of silica-zirconia composite oxide particles was weighed; the dispersion was dried at 100° C. for 12 hours in an oven; then, the mass after drying was weighed. The concentration of particles in the dispersion was calculated using the following formula.

(Concentration of particles after drying/weight of liquid dispersion of silica-zirconia composite oxide particles)×100(%)

(6) Concentration of Acetonitrile

The before-reaction concentration of acetonitrile was calculated using the amount of acetonitrile fed. With respect to the after-reaction concentration of acetonitrile, the obtained liquid dispersion of silica-zirconia composite oxide particles was subjected to centrifugation to obtain a filtrate; and the filtrate was analyzed using high-performance liquid chromatography. The analysis data was converted to mass using the specific gravity of acetonitrile, whereby the concentration of acetonitrile in reaction solvent was determined. Using the concentration of particles calculated in the above (5), there was determined the concentration of acetonitrile in the total liquid dispersion of silica-zirconia composite oxide particles.
(7) Dispersion of Particles 3 g of a liquid dispersion of silica-zirconia composite oxide particles, obtained by the reaction was taken, then placed in a 10-ml sample tube, and allowed to stand for 30 seconds. At this time, the state in which the dispersion separated into a liquid and a precipitate, was examined visually. A case that the precipitate of separated particles was confirmed even if the amount was minor, was taken as "precipitation". When there was no precipitation, one drop of the liquid dispersion was dropped on the sample plate of a scanning electron microscope and dried. Then, the dried particles were observed at a magnification at which at least 200 primary particles could be observed in the field of the scanning electron microscope. A case that there was no coagulation of two or more particles and all particles were in mono-dispersion, was taken as "E"; a case that the coagulation of two or more particles was observed slightly, was taken as "G"; and a case that the coagulation of two or more particles was observed in a large amount, was taken as "B".

Example 1

Preparation of Alkoxide Solution for Production of Composite Oxide Particles

Into a 2-liter Erlenmeyer flask were fed 356 g of tetraethoxysilane (Colcoat Co., Ltd.) and 427 g of isobutyl alcohol, followed by stirring. Thereinto was added 8.9 g of dilute sulfuric acid (0.06% by mass), followed by stirring for 17 hours to conduct the partial hydrolysis of tetraethoxysilane. Successively, to the reaction mixture obtained were added 114 g of tetra-butyl zirconate (Hokko Chemical Industry Co., Ltd., trade name: HZ-NB) and 17.3 g of 28% sodium methoxide (Wako Pure Chemical Industries, ltd.) to obtain a colorless, transparent alkoxide solution for production of composite oxide particles.
(Production of Silica-Zirconia Composite Oxide Particles)

Into a jacket-fitted, glass-made reactor (internal volume: 3 liters) provided with an agitating element were fed 370 g of acetonitrile, 107 g of isobutyl alcohol and 260 g of ammonia water (25% by mass). The temperature of the circulation water in the jacket was set at 40° C., and the agitating element was rotated at 180 rpm to stir the inside of the reactor. Then, to the thus-prepared reaction solvent was added the total amount (923.2 g) of the alkoxide solution for production of composite oxide particles, prepared previously, in 7 hours. Then, stirring was made for 20 minutes to obtain a liquid dispersion of silica-zirconia composite oxide particles.

The liquid dispersion of silica-zirconia composite oxide particles was measured for particles concentration, which was 12% by mass. The formed silica-zirconia composite oxide particles had a composition of $SiO_2$=83.3 mol %, $ZrO_2$=14.5 mol % and $Na_2O$=2.2 mol % when calculated form the amounts of raw materials fed.

Part of the particles was taken out and subjected to conduct image analysis. The average particle diameter was 0.15 μm, the fluctuation coefficient of particle diameters was 6.0%, and the roundness of particles was 0.9. Also, the dispersion of the particles was examined, which was "E". In this reaction for production of silica-zirconia composite oxide particles, the acetonitrile concentration in reaction mixture at the start of reaction was 50% by mass, and the acetonitrile concentration in reaction mixture at the completion of reaction was 22% by mass.
(Coating with Silica Layer)

Into a 1-liter Erlenmeyer flask were fed 89.3 g of tetraethoxysilane (Colcoat Co., Ltd.) and 300 g of methyl alcohol, followed by stirring to prepare an alkoxide solution for silica coating. The total amount of the obtained alkoxide solution for silica coating was dropped into the above-produced liquid dispersion of silica-zirconia composite oxide particles by in-liquid dropping with stirring, in 2 hours. Stirring was continued for 20 minutes after the dropping. The acetonitrile concentration at the completion of the reaction was 17% by mass.

There was obtained, by the above reaction, a liquid high-dispersion of silica-zirconia composite oxide particles each coated with a silica layer. The dispersed silica-zirconia composite oxide particles each coated with a silica layer were observed using a scanning electron microscope. The shape of particles was spherical and neither particle adhesion nor particle coagulation was observed. Image analysis was conducted. The average particle diameter was 0.15 μm, the fluctuation coefficient of particle diameters was 6.0% and the roundness of particles was 0.90. The thickness of coated silica layer was 10 nm.

The dispersion of particles was examined, which was "E". Then, the silica-zirconia composite oxide particles each coated with a silica layer were allowed to coagulate and precipitate, filtered and dried. A part of the dried particles was fired at 880° C. for 5 hours. The fired particles were observed using a scanning electron microscope. As a result, the average particle diameter was found to be smaller by about 8%. Other properties were about the same as mentioned above and there was no change. The refractive index of particles was 1.54. X-ray diffraction indicated that the dried particles and the fired particles were both nearly amorphous.

Example 2

Preparation of Alkoxide Solution for Production of Composite Oxide Particles

Into a 3-liter Erlenmeyer flask were fed 786 g of tetraethoxysilane (Colcoat Co., Ltd.) and 444 g of isobutyl alcohol, followed by stirring. Thereinto was added 22.2 g of dilute sulfuric acid (0.06% by mass) to conduct the partial hydrolysis of tetraethoxysilane for 17 hours. Successively, to the reaction mixture obtained were added 228 g of tetra-butyl zirconate (Hokko Chemical Industry Co., Ltd., trade name: HZ-NB) and 34.6 g of 28% sodium methoxide (Wako Pure Chemical Industries, ltd.) to obtain a colorless, transparent alkoxide solution for production of composite oxide particles.
(Production of Silica-Zirconia Composite Oxide Particles)

Into a jacket-fitted, glass-made reactor (internal volume: 3 liters) provided with an agitating element were fed 300 g of acetonitrile and 280 g of ammonia water (25% by mass). The temperature of the circulation water in the jacket was set at 40° C. The agitating element was rotated at 180 rpm for stirring. Then, to the thus-prepared reaction solvent was fed 1514.8 g (total amount) of the alkoxide solution for production of composite oxide particles, prepared previously, in 7 hours. Then, the reaction mixture was stirred for 20 minutes.

By the above reaction was obtained a liquid dispersion of silica-zirconia composite oxide particles. The liquid dispersion was measured for particles concentration, which was 19%. The formed silica-zirconia composite oxide particles had a composition of $SiO_2$=83.3 mol %, $ZrO_2$=14.5 mol % and $Na_2O$=2.2 mol % when calculated form the amounts of raw materials fed.

Part of the particles was taken out and subjected to image analysis. The average particle diameter was 0.15 μm, the fluctuation coefficient of particle diameters was 7.2%, and the roundness of particles was 0.7. Also, the dispersion of the particles was examined, which was "G". In this reaction for production of silica-zirconia composite oxide particles, the acetonitrile concentration in reaction mixture at the start of reaction was 52% by mass, and the acetonitrile concentration in reaction mixture at the completion of reaction was 14% by mass.
(Coating with Silica Layer)

Into a 1-liter Erlenmeyer flask were fed 268 g of tetraethoxysilane (Colcoat Co., Ltd.) and 500 g of methyl alcohol, followed by stirring to prepare an alkoxide solution for silica coating. The obtained alkoxide solution for silica coating was dropped to the above-produced liquid dispersion of silica-zirconia composite oxide particles in 5 hours. Stirring was continued for 20 minutes after the dropping. The acetonitrile concentration at the completion of reaction was 8% by mass.

There was obtained, by the above reaction, a liquid high-dispersion of silica-zirconia composite oxide particles each coated with a silica layer. The dispersed silica-zirconia composite oxide particles each coated with a silica layer were observed using a scanning electron microscope. The shape of particles was spherical and particle adhesion was seen slightly. Image analysis was conducted. The average particle diameter was 0.15 μm, the fluctuation coefficient of particle diameters was 7.2% and the roundness of particles was 0.7. The dispersion of particles was examined, which was "E".

The thickness of coated silica layer was 9 nm. Then, the silica-zirconia composite oxide particles each coated with a silica layer were allowed to coagulate, precipitate and filtered. Part of the dried particles was fired at 860° C. for 6 hours. The fired particles were observed using a scanning electron microscope. As a result, the average particle diameter was found to be smaller by about 7%. Other properties were about the same as mentioned above. The refractive index of particles was 1.54. X-ray diffraction indicated that the dried particles and the fired particles were both nearly amorphous.

Example 3

Preparation of Alkoxide Solution for Production of Composite Oxide Particles

There was used the same alkoxide solution for production of composite oxide particles, as used in Example 1.
(Production of silica-zirconia composite oxide particles)

Into a jacket-fitted, glass-made reactor (internal volume: 3 liters) provided with an agitating element were fed 477 g of acetonitrile and 260 g of ammonia water (25% by mass). The temperature of the circulation water in the jacket was set at 40° C. The agitating element was rotated at 180 rpm to stir the inside of the reactor. To the thus-prepared reaction solvent was fed 923.2 g (total amount) of the alkoxide solution for production of composite oxide particles, prepared previously, in 7 hours. Then, the reaction mixture was stirred for 20 minutes.

By the above reaction was obtained a liquid dispersion of silica-zirconia composite oxide particles. The particles concentration in the dispersion was 11% by mass. The dispersion of particles was examined, which was "E". The formed silica-zirconia composite oxide particles had a composition of $SiO_2$=83.3 mol %, $ZrO_2$=14.5 mol % and $Na_2O$=2.2 mol % when calculated form the amounts of raw materials fed.

Part of the particles was taken out and subjected to image analysis. The average particle diameter was 0.15 μm, the fluctuation coefficient of particle diameters was 6.2%, and the roundness of particles was 0.8. In this reaction for production of silica-zirconia composite oxide particles, the acetonitrile concentration in reaction mixture at the start of reaction was 65% by mass, and the acetonitrile concentration in reaction mixture at the completion of reaction was 29% by mass.
(Coating with Silica Layer)

Into a 1-liter Erlenmeyer flask were fed 89.3 g of tetraethoxysilane (Colcoat Co., Ltd.) and 300 g of acetonitrile, followed by stirring to prepare an alkoxide solution for silica coating. The total amount of the obtained alkoxide solution for silica coating was dropped into the above-produced liquid dispersion of silica-zirconia composite oxide particles by in-liquid dropping in 2 hours, with stirring.

The acetonitrile concentration at the completion of reaction was 38% by mass.

There was obtained, by the above reaction, a liquid high-dispersion of silica-zirconia composite oxide particles each coated with a silica layer. The dispersed silica-zirconia composite oxide particles each coated with a silica layer were observed using a scanning electron microscope. The shape of particles was spherical and neither adhesion nor particles coagulation was observed. Image analysis was conducted. The average particle diameter was 0.15 μm, the fluctuation coefficient of particle diameters was 6.2% and the roundness of particles was 0.8. The thickness of silica layer was 10 nm. The dispersion of particles was examined, which was "E". Then, the silica-zirconia composite oxide particles each coated with a silica layer were allowed to coagulate and precipitate, filtered and dried. Part of the dried particles was fired at 880° C. for 5 hours. The fired particles were observed using a scanning electron microscope. As a result, the average particle diameter was found to be smaller by about 8%. Other properties were about the same as mentioned above and there was no change. The refractive index of particles was 1.54. X-ray diffraction indicated that the dried particles and the fired particles were both nearly amorphous.

Examples 4 to 10

Silica-zirconia composite oxide particles each coated with a silica layer were produced using the same operation as in Example 1 except that the reaction conditions shown in Table 1 and Table 2 were used. The results are shown in Table 1 and Table 2.

Comparative Example 1

Preparation of Alkoxide Solution for Production of Composite Oxide Particles

Into a 2-liter Erlenmeyer flask were fed 518 g of tetramethoxysilane (Colcoat Co., Ltd.) and 160 g of methanol, followed by stirring. Thereinto was added 8.9 g of dilute sulfuric acid (0.06% by mass) and the partial hydrolysis of tetraethoxysilane was conducted for 17 hours, with stirring. Successively, 170.5 g of titanium tetra-isopropoxide (Nippon Soda Co., Ltd., trade name: A-1) was added to obtain a colorless, transparent alkoxide solution for production of composite oxide particles.
(Production of Silica-Titania Composite Oxide Particles)

Into a jacket-fitted, glass-made reactor (internal volume: 3 liters) provided with an agitating element were fed 667 g of acetonitrile and 133 g of ammonia water (25% by mass). The temperature of the circulation water in the jacket was set at 40° C. The agitating element was rotated at 180 rpm to stir the inside of the reactor. Then, to the thus-prepared reaction solvent was fed the total amount (857.4 g) of the alkoxide solution for production of composite oxide particles, prepared previously, in 7 hours. Then, stirring was made for 20 minutes to obtain a liquid dispersion of silica-titania composite oxide particles.

The liquid dispersion of silica-titania composite oxide particles was measured for particles concentration, which was 15% by mass. The formed silica-titania composite oxide particles had a composition of $SiO_2$=85.0 mol % and $TiO_2$=15.0 mol % when calculated form the amounts of raw materials fed.

Part of the particles was taken out and subjected to image analysis. The average particle diameter was 0.20 μm, the fluctuation coefficient of particle diameters was 5.2%, and the roundness of particles was 0.9. The dispersion of the particles was examined, which was "E". In this reaction for production of silica-titania composite oxide particles, the acetonitrile concentration in reaction mixture at the start of reaction was 83% by mass, and the acetonitrile concentration in reaction mixture at the completion of reaction was 48% by mass.

(Coating with Silica Layer)

Into a 1-liter Erlenmeyer flask were fed 89.3 g of tetraethoxysilane (Colcoat Co., Ltd.) and 300 g of MeOH, followed by stirring to prepare an alkoxide solution for silica coating. The obtained alkoxide solution for silica coating was dropped to the above-produced liquid dispersion of silica-titania composite oxide particles. Striking coagulation of particles was seen about 1 hour after the start of the dropping. As a result, there was no particle of mono-dispersion Comparative Example 2

Production of silica-alumina composite oxide particles each coated with a silica layer was tried using the same operation as in Example 1 except that, in the step of (preparation of alkoxide solution for production of composite oxide particles) of Example 1, 114 g of tetra-butyl zirconate was replaced by the same mols (41 g) of aluminum ethoxide (Reagent of Wako Pure Chemical Industries, Ltd.).

However, in the step of (preparation of silica-alumina composite oxide particles), there was seen, after about 1 hour from the start of the dropping of an alkoxide solution for production of composite oxide particles, striking coagulation of the silica-alumina composite oxide particles formed in the reaction mixture, and no particle of mono-dispersion was obtainable.

Comparative Example 3

Preparation of Composite Alkoxide Solution

The same operation as in Example 1 was repeated. That is, into a 2-liter Erlenmeyer flask were fed 356 g of tetraethoxysilane (Colcoat Co., Ltd.) and 427 g of isobutyl alcohol, followed by stirring. Thereinto was added 8.9 g of dilute sulfuric acid (0.06% by mass) to conduct the partial hydrolysis of tetraethoxysilane for 17 hours. Successively, to the reaction mixture obtained were added 114 g of tetra-isobutyl zirconium (Hokko Chemical Industry Co., Ltd., trade name: HZ-NB) and 17.3 g of 28% sodium methoxide (Wako Pure Chemical Industries, ltd.) to obtain a colorless, transparent composite alkoxide solution.

(Production of Silica-Based Composite Oxide Particles)

Into a jacket-fitted, glass-made reactor (internal volume: 3 liters) provided with an agitating element were fed 130 g of acetonitrile, 200 g of isobutyl alcohol (IBA) and 360 g of ammonia water (25% by mass). The temperature of the circulation water in the jacket was set at 40° C. and rotated the agitating element at 180 rpm. Then, to the thus-prepared reaction solvent was fed the total amount (923.2 g) of the above-prepared composite alkoxide solution in 7 hours.

By the above reaction was obtained a liquid dispersion of silica-zirconia composite oxide particles. The liquid dispersion was measured for particles concentration, which was 11% by mass. The formed silica-zirconia composite oxide particles had a composition of $SiO_2$=83.3 mol %, $ZrO_2$=14.5 mol % and $Na_2O$=2.2 mol % when calculated form the amounts of raw materials fed.

Part of the particles was taken out and subjected to image analysis. The average particle diameter was 0.14 μm, the fluctuation coefficient of particle diameters was 6.5%, and the roundness of particles was 0.8. Also, the dispersion of the particles was examined, which was "G". In this reaction for production of silica-zirconia composite oxide particles, the acetonitrile concentration in reaction mixture at the start of reaction was 19% by mass, and the acetonitrile concentration in reaction mixture at the completion of reaction was 8% by mass.

(Coating with Silica Layer)

Into a 1-liter Erlenmeyer flask were fed 89.3 g of tetraethoxysilane (Colcoat Co., Ltd.) and 300 g of methyl alcohol, followed by stirring. The thus-prepared reaction mixture was dropped to the above-produced liquid dispersion of silica-based composite oxide particles in 2 hours. Striking coagulation of particles was seen after about 1 hour from the start of the dropping. As a result, there was no particle of mono-dispersion.

TABLE 1

| | | Reaction for producing silica-zirconia composite oxide particles | | | | | | | | | | |
|---|---|---|---|---|---|---|---|---|---|---|---|---|
| | Examples | | 1 | 2 | 3 | 4 | 5 | 6 | 7 | 8 | 9 | 10 |
| Composition of Silica-zirconia composite oxide particles | $SiO_2$ | mol % | 83.3 | 83.3 | 83.3 | 86.5 | 86.5 | 81 | 81 | 83.3 | 85.8 | 86.8 |
| | $ZrO_2$ | mol % | 14.5 | 14.5 | 14.5 | 12.5 | 12.5 | 16.9 | 16.9 | 14.5 | 14.2 | 11.4 |
| | $Na_2O$ | mol % | 2.2 | 2.2 | 2.2 | 1.5 | 1.5 | 2.1 | 2.1 | 2.2 | | 1.8 |
| Liquids fed | Isobutyl alcohol | g | 107 | | | 110 | 110 | 110 | 110 | 100 | | |
| | Acetonitrile | g | 370 | 300 | 477 | 350 | 350 | 300 | 300 | 450 | 300 | 450 |
| | Aq. 25% $NH_3$ | g | 260 | 300 | 260 | 280 | 280 | 260 | 400 | 280 | 280 | 280 |
| Particles concentration at completion of reaction | | mass % | 11 | 19 | 11 | 11 | 16 | 13 | 15 | 7 | 13 | 13 |
| Acetonitrile concentration at start of reaction | | mass % | 50 | 52 | 65 | 47 | 47 | 45 | 37 | 54 | 52 | 52 |
| Acetonitrile concentration at completion of reaction | | mass % | 22 | 14 | 29 | 17 | 15 | 20 | 11 | 37 | 20 | 20 |
| Properties of silica-zirconia composite oxide | Average particle diameter | μm | 0.15 | 0.15 | 0.15 | 0.15 | 0.15 | 0.13 | 0.42 | 0.2 | 0.14 | 0.14 |

TABLE 1-continued

Reaction for producing silica-zirconia composite oxide particles

| | Examples | | 1 | 2 | 3 | 4 | 5 | 6 | 7 | 8 | 9 | 10 |
|---|---|---|---|---|---|---|---|---|---|---|---|---|
| particles | Fluctuation coefficient | % | 6 | 7.2 | 6.2 | 6.4 | 7.4 | 6.6 | 6.5 | 5.4 | 6.3 | 6.3 |
| | Roundness | | 0.9 | 0.7 | 0.8 | 0.8 | 0.7 | 0.8 | 0.7 | 0.9 | 0.8 | 0.8 |
| Dispersion of particles | | | E | G | E | E | G | E | G | E | E | E |

TABLE 2

Reaction for forming a coated silica layer

| | Examples | | 1 | 2 | 3 | 4 | 5 | 6 | 7 | 8 | 9 | 10 |
|---|---|---|---|---|---|---|---|---|---|---|---|---|
| Alkoxide solution for silica coating | TES | g | 89.3 | 268 | 89.3 | 300 | 60 | 49 | 268 | 49 | 89.3 | 89.3 |
| | Acetonitrile | g | — | — | 300 | — | — | 165 | 500 | — | — | — |
| | Methanol | g | 300 | 500 | — | 900 | 300 | — | — | 150 | 300 | 300 |
| Acetonitrile concentration at completion of reaction | Mass % | | 17 | 10 | 37 | 11 | 12 | 26 | 22 | 31 | 15 | 15 |
| Properties of silica-zirconia composite oxide particles each coated with a silica layer | Average particle diameter | μm | 0.15 | 0.15 | 0.15 | 0.16 | 0.15 | 0.13 | 0.42 | 0.14 | 0.20 | 0.14 |
| | Coated thickness | nm | 10 | 9 | 10 | 25 | 6 | 11 | 15 | 7 | 10 | 13 |
| | Refractive index | nD | 1.54 | 1.54 | 1.54 | 1.52 | 1.52 | 1.54 | 1.54 | 1.54 | 1.54 | 1.51 |
| | Fluctuation coefficient | % | 6.0 | 7.2 | 6.2 | 6.4 | 7.4 | 6.6 | 6.5 | 6.3 | 5.4 | 5.1 |
| | Roundness | | 0.9 | 0.7 | 0.8 | 0.8 | 0.7 | 0.8 | 0.8 | 0.9 | 0.8 | 0.9 |
| Dispersion of particles | | | E | G | E | E | G | E | G | E | E | E |

TES: Tetraethoxysilane

TABLE 3

Reaction for producing silica-based composite oxide particles

| | Comparative Examples | | 1 | 2 | 3 |
|---|---|---|---|---|---|
| Composition of silica-based composite oxide particles | SiO$_2$ | mol % | 85.0 | 83.3 | 83.3 |
| | ZrO$_2$ | mol % | — | — | 14.5 |
| | TiO$_2$ | mol % | 15.0 | — | — |
| | Al$_2$O$_3$ | mol % | — | 14.5 | — |
| | Na$_2$O | mol % | — | 2.2 | 2.2 |
| Liquids fed | Isobutyl alcohol | g | — | 107 | 200 |
| | Acetonitrile | g | 677 | 370 | 130 |
| | Methanol | g | — | — | — |
| | Aq. 25% NH$_3$ | g | 133 | 260 | 360 |
| Particles concentration at completion of reaction | Mass % | | 15 | — | 13 |
| Acetonitrile concentration at start of reaction | Mass % | | 83 | — | 19 |
| Acetonitrile concentration at completion of reaction | Mass % | | 48 | — | 8 |
| Properties of silica-based composite oxide particles | Average particle diameter | μm | 0.20 | — | 0.14 |
| | Fluctuation coefficient | % | 5.2 | — | 6.7 |
| | Roundness | | 0.9 | — | 0.8 |
| Dispersion of particles | | | E | Precipitation | G |

TABLE 4

Reaction for forming a coated silica layer

| | Comparative Examples | | 1 | 2 | 3 |
|---|---|---|---|---|---|
| Feeding for coated silica layer | TES | g | 89.3 | — | 89.3 |
| | Acetonitrile | g | — | — | — |
| | Methanol | g | 300 | — | 300 |
| Acetonitrile concentration at completion of reaction | Mass % | | — | — | — |
| Properties of silica-based composite oxide particles each coated with a silica layer | Average particle diameter | μm | — | — | — |
| | Coated thickness | nm | — | — | — |
| | Refractive index | nD | — | — | — |
| | Fluctuation coefficient | % | — | — | — |
| | Roundness | | — | — | — |
| Dispersion of particles | | | Precipitation | — | Precipitation |

The invention claimed is:

1. A method for producing silica-zirconia composite oxide particles each coated with a silica layer, comprising the steps of reacting an alkoxide of silicon and/or a condensable compound derived from the alkoxide with an alkoxide of zirconium and/or a condensable compound derived from the alkoxide in a water-containing solvent that contains acetonitrile so that the reaction mixture contains at least 10% by mass of acetonitrile, to produce a liquid dispersion of silica-zirconia composite oxide particles dispersed in the reaction mixture at 5 to 30% by mass, and then reacting the silica-zirconia composite oxide particles dispersed in the said liquid dispersion containing at least 10% by mass of acetonitrile with an alkoxide of silicon and/or a condensable compound derived from the alkoxide in the liquid dispersion of silica-zirconia composite oxide particles to coat the surface of each silica-zirconia composite oxide particle with a silica layer.

2. The method for producing silica-zirconia composite oxide particles each coated with a silica layer, according to claim 1, wherein the silica-zirconia composite oxide particles dispersed in the liquid dispersion of silica-zirconia composite oxide particles have an average particle diameter of 0.05 to 1.0 μm.

3. The method for producing silica-zirconia composite oxide particles coated with a silica layer, according to claim 2, wherein the silica layer coated on the surface of each silica-zirconia composite oxide particle has a thickness of 5 to 30 nm.

4. A method for producing silica-zirconia composite oxide particles each coated with a silica layer, used as a filler for dental composite resin, which method comprising the steps of: reacting an alkoxide of silicon and/or a condensable compound derived from the alkoxide with an alkoxide of zirconium and/or a condensable compound derived from the alkoxide in a water-containing solvent that contains acetonitrile so that the reaction mixture contains at least 10% by mass of acetonitrile, to produce a liquid dispersion of silica-zirconia composite oxide particles dispersed in the reaction mixture at 5 to 30% by mass, and then reacting the silica-zirconia composite oxide particles dispersed in the liquid dispersion containing at least 10% by mass of acetonitrile with an alkoxide of silicon and/or a condensable compound derived from the alkoxide in the liquid dispersion of silica-zirconia composite oxide particles, to coat the surface of each silica-zirconia composite oxide particle with a silica layer.

\* \* \* \* \*